(12) United States Patent
Xu et al.

(10) Patent No.: US 11,827,667 B2
(45) Date of Patent: Nov. 28, 2023

(54) PRODUCTION METHOD FOR GUANOSINE DERIVATIVE HAVING FLUORINE ATOM-CONTAINING FUNCTIONAL GROUP AT POSITION 8 AND APPLICATION THEREOF

(71) Applicant: UNIVERSITY OF MIYAZAKI, Miyazaki (JP)

(72) Inventors: Yan Xu, Miyazaki (JP); Takumi Ishizuka, Miyazaki (JP); Hong-Liang Bao, Miyazaki (JP)

(73) Assignee: UNIVERSITY OF MIYAZAKI, Miyazaki (JP)

( * ) Notice: Subject to any disclaimer, the term of this patent is extended or adjusted under 35 U.S.C. 154(b) by 0 days.

(21) Appl. No.: 17/275,083

(22) PCT Filed: Aug. 29, 2019

(86) PCT No.: PCT/JP2019/033875
§ 371 (c)(1),
(2) Date: Mar. 10, 2021

(87) PCT Pub. No.: WO2020/054444
PCT Pub. Date: Mar. 19, 2020

(65) Prior Publication Data
US 2021/0261595 A1    Aug. 26, 2021

(30) Foreign Application Priority Data

Sep. 14, 2018 (JP) ................................. 2018-172013

(51) Int. Cl.
*C07H 19/167* (2006.01)
*C07H 19/173* (2006.01)

(52) U.S. Cl.
CPC ......... *C07H 19/167* (2013.01); *C07H 19/173* (2013.01)

(58) Field of Classification Search
None
See application file for complete search history.

(56) References Cited

U.S. PATENT DOCUMENTS

2009/0124796 A1    5/2009  Yamakawa et al.

FOREIGN PATENT DOCUMENTS

| JP | 2010-60394 A | 3/2010 |
|---|---|---|
| WO | 2007/055170 A1 | 5/2007 |

OTHER PUBLICATIONS

Firth, Tetrahedron Letters 47 (2006) 3529-3533. (Year: 2006).*
Sono, Chem. Pharm. Bull. 44(6) 1141-1145 (1996). (Year: 1996).*
Registry No. 1186428-82-8, which entered STN on Sep. 29, 2009. (Year: 2009).*
International Search Report (ISR) dated Nov. 19, 2019 filed in PCT/JP2019/033875.
Xu et al., "8-Methylguanosine: A powerful Z-DNA Stabilizer", Journal of the American Chemical Society, 2003, vol. 125, No. 44, pp. 13519-13524; Cited in Specification.
Musumeci et al., "Trifluoromethyl derivatives of canonical nucleosides: synthesis and bioactivity studies", Medicinal Chemistry Communication, 2013, vol. 4, pp. 1405-1410; Cited in Specification & ISR.
Yoshimura et al., "Ultrafast Reversible Photo-Cross-Linking Reaction: Toward in Situ DNA Manipulation", Organic Letters, 2008, vol. 10, No. 15, pp. 3227-3230; Cited in Specification; English text.
Kore et al., "Efficient synthesis of 3-cyanovinylcarbazole-1'-b-deoxyriboside-5'-triphosphate: a reversible photo-cross-linking probe", Tetrahedron Letters 53, Elsevier, 2012, pp. 4012-4014; Cited in Specification.
Rublack et al., "Synthesis of Specifically Modified Oligonucleotides for Application in Structural and Functional Analysis of RNA", Journal of Nucleic Acids, 2011, vol. 2011, pp. 1-19, Fig. 4-5, table 4, etc.; Cited in ISR.
Saito et al., "C8-alkynyl- and alkylamina substituted 2'-deoxyguanosines: a universal linker for nucleic acids modification", ScienceDirect, Tetrahedron 64, Elseview, 2008, pp. 3578-3588, scheme 2, Fig.2, etc; Cited in ISR.
Kapmeyer et al., "The synthesis of 8-(6-aminohexyl)-amino-GTP and -GDP and Their Application as Ligands in Affinity Chromatography", Analytical Biochemistry 99, 1979, pp. 189-199, Fig. 1, etc.; Cited in ISR.
Pflederer et al., "Synthesis and Structure of 8-Methyl- and 8-Trifluoromethyl-guanine-Nucleosides", Chemische Berichte, 1972. vol. 105, No. 5, pp. 1497-1509, p. 1498, Fig. 3, 6, etc.; Cited in ISR.
Namavari et al., "Synthesis of 8-[18F] Fluoroguanine Derivatives: In Vivo Probes for Imaging Gene Expression with Positron Emission Tomography", Nuclear Medicine and Biology, 2000, vol. 27, No. 2, pp. 157-162, Fig. 3, table 1, etc.; Cited in ISR.
Bao et al., "Improving Thermodynamic Stability and Anticoagulant Activity of a Thrombin Binding Aptamer by Incorporation of 8-trifluoromethyl-2'-deoxyguanosine", Journal of Medicinal Chemistry, 2021, vol. 64, No. 1, pp. 711-718, By Applicant.
Bao et al., "Oligonucleotides DNA containing, 8-trifluoromethyl-2'-deoxyguanosine for observing Z-DNA structure", Nucleic Acid Research, 2020, vol. 48, No. 13, pp. 7041-7051, By Applicant.

* cited by examiner

*Primary Examiner* — Layla D Berry
(74) *Attorney, Agent, or Firm* — Rankin, Hill & Clark LLP

(57) ABSTRACT

[Problem] To develop a technique that can stabilize the higher-order structure of a nucleic acid and can be used in analysis of nucleic acid structure. [Solution] This guanosine derivative compound is represented by formula 1. In the formula, one of $R_1$ and $R_2$ represents H, and the other represents any of H, OH, $OCH_3$, and F, $R_3$ represents a functional group that is for detection and that has $^{19}F$, $R_4$ represents an amine-protecting group, $R_5$ represents a hydroxy group-protecting group, and $R_6$ represents an introduction group that is to be introduced into a nucleic acid oligomer. This guanosine derivative compound can be introduced as a part of a nucleic acid sequence, and the introduced nucleic acid oligomer stabilizes the higher-order structure in a nucleic acid, and enables dynamic detection by $^{19}F$ NMR.

8 Claims, 8 Drawing Sheets
Specification includes a Sequence Listing.

a, CD spectra of ODN1. Condition: 20 μM DNA and 1 mM Na-PO$_4$ buffer (pH 7.0) in various concentrations of NaCl. b, Profiles of the absorbance at 295 nm versus NaCl concentration.

CD spectra of ODN2 and ODN5. Condition: 25 μM DNA and 1 mM Na-PO$_4$ buffer (pH 7.0) in various concentrations of NaCl. (b) Profiles of the absorbance at 295 nm versus NaCl concentration.

CD (a) and CD melting (b) spectra of ODN4 and ODN8. Condition: 10 μM DNA in 100 mM KCl and 20 mM K-PO₄ buffer (pH 7.0).

CD (a) and CD melting (b) spectra of ODN3/ODN7 and ODN6/ODN7. Condition: 10 μM DNA in 100 mM KCl and 20 mM K-PO₄ buffer (pH 7.0).

FIG. 10

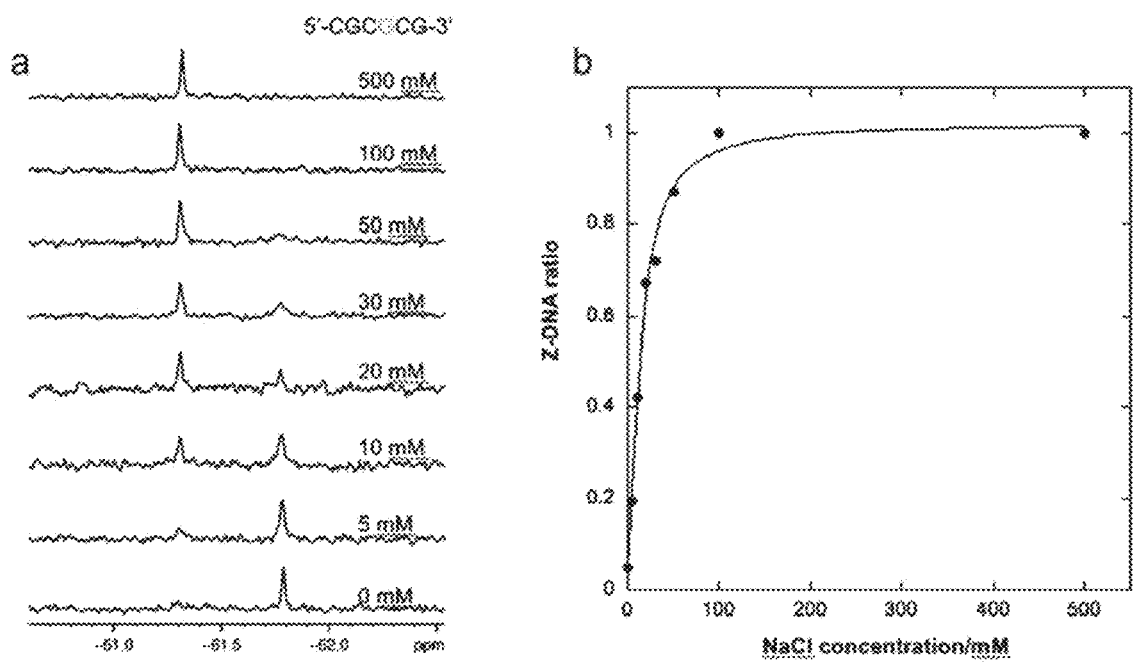

a, $^{19}$F NMR spectra of ODN1. Condition: 25 μM duplex DNA and 1 mM Na-PO$_4$ buffer (pH 7.0) in various concentrations of NaCl. b, Profiles of the Z-DNA ratio obtained from the integration of $^{19}$F NMR signals versus NaCl concentrations.

FIG. 11

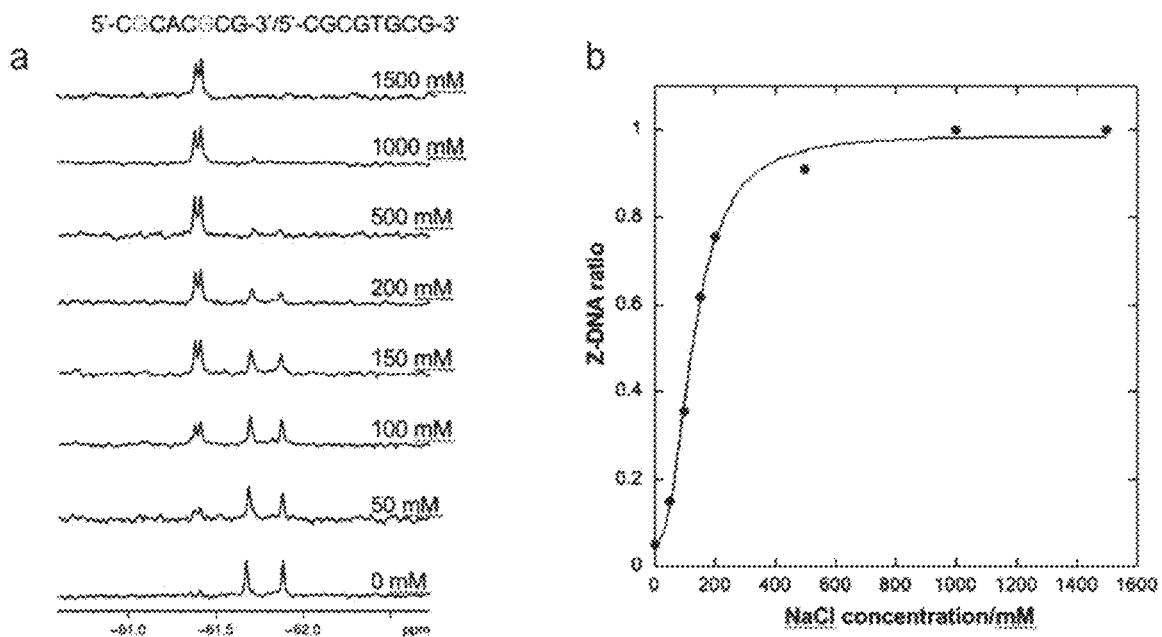

a, $^{19}$F NMR spectra of ODN2 and ODN5. Condition: 50 μM duplex DNA consisted of 1:1 mixture by ODN2 and ODN1 with 1 mM Na-PO$_4$ buffer (pH 7.0) in various concentrations of NaCl. b, Profiles of the Z-DNA ratio obtained from the integration of $^{19}$F NMR signals versus NaCl concentrations.

FIG. 12

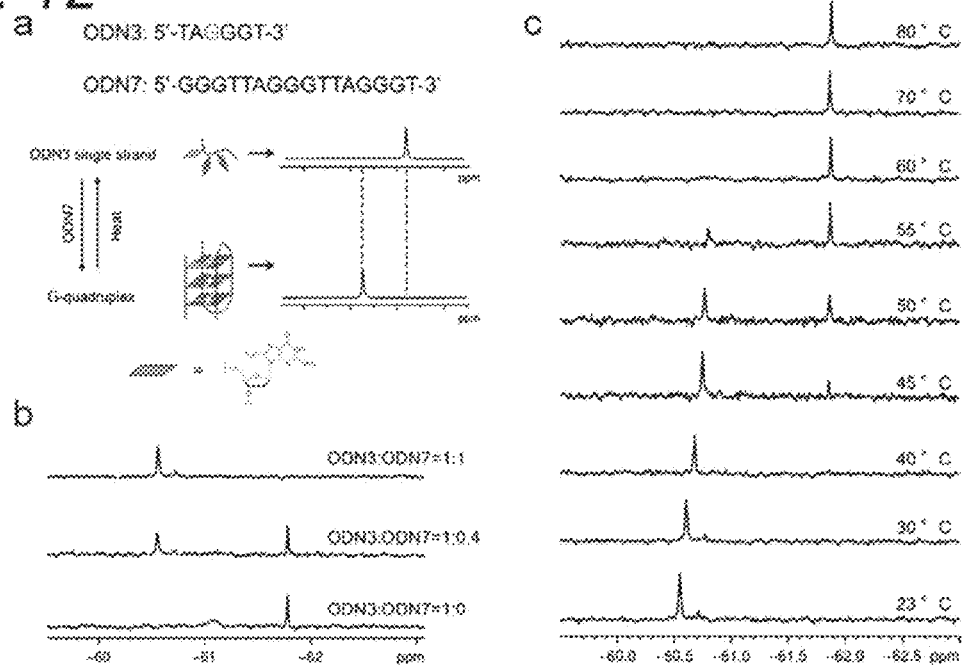

a, Concept for the detection G-quadruplex structures by $^{19}$F NMR. b, $^{19}$F NMR spectra of ODN3 and ODN7. Condition: 200 μM concentration of ODN3 and various concentrations of ODN7 (0-200 μM) in 100 mM KCl and 20 mM K-PO$_4$ buffer (pH 7.0). c, $^{19}$F NMR spectra of ODN3 and ODN7 in different temperatures. Condition: 200 μM concentration of duplex DNA consisted of 1:1 mixture by ODN3 and ODN7 in 100 mM KCl and 20 mM K-PO$_4$ buffer (pH 7.0)

FIG. 13

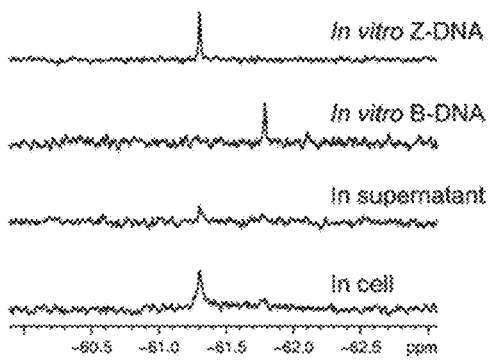

$^{19}$F NMR spectra of ODN1 in Hela cell, in supernatant, and two upper spectra indicated the chemical shift of Z form DNA and B form DNA *in vitro*.

FIG. 14
HE STAINING

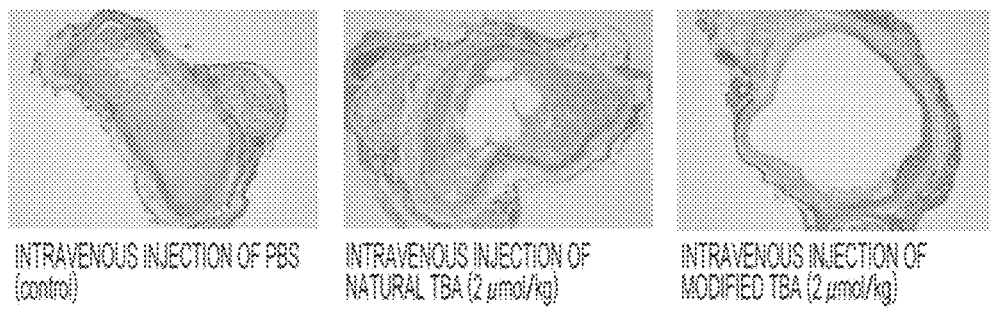

PRODUCTION METHOD FOR GUANOSINE DERIVATIVE HAVING FLUORINE ATOM-CONTAINING FUNCTIONAL GROUP AT POSITION 8 AND APPLICATION THEREOF

TECHNICAL FIELD

The present disclosure relates to guanosine derivatives.

BACKGROUND ART

DNA is composed of four types of nucleobases, adenine, thymine, guanine, and cytosine, and is known to have a double helix structure consisting of two polynucleotide chains as a basic structure. In addition, it has become clear that DNA has a complex higher-order structure, and that this higher-order structure regulates the on/off of functions. It is also known that RNA also changes its secondary structure by folding.
From these facts, it is extremely important for the analysis of biological functions and drug development to dynamically analyze the higher-order structure of nucleic acids and clarify their functions. Various techniques for this purpose are disclosed (Patent Document 1, Non-Patent Documents 1 and 2).

CITATION LIST

Patent Literature

Patent Documents 1: International release2007/055170 pamphlet

Non Patent Literature

Non Patent Literature 1: Yan Xu, Reiko Ikeda, Hiroshi Sugiyama "8-Methylguanosine: a powerful Z-DNA stabilizer" J. Am. Chem. Soc. 2003 125, 13519-13524.
Non Patent Literature 2: Domenica Musumeci, Carlo Trace, Rita Santamaria, Daniela Montesarchio "Trifluoromethyl derivatives of canonical nucleosides: synthesis and bioactivity studies" Med. Chem. Commun. 2013, 4, 1405-1410.
Non Patent Literature 3: Yoshinaga Yoshimura, Kenzo Fujimoto "Ultrafast Reversible Photo-Cross-Linking Reaction: Toward in Situ DNA Manipulation" Org. Lett. 2008, 10, 3227-3230.
Non Patent Literature 4: Anilkumar R. Kore, Balasubramanian Srinivasan "Efficient synthesis of 3-cyanovinylcarbazole-1'-β-deoxyriboside-5'-triphosphate: a reversible photo-cross-linking probe" Tetrahedron Lett. 2012, 53, 4012-4014.

INVENTION DISCLOSURE

Technical Problem

Technology related to nucleobases having perfluoroalkyl groups and their production methods are disclosed in non-patent literature 1.
Technology related to compounds for stabilizing the structure of Z-DNA is disclosed in non-patent literature 2.
A method for producing trifluoromethyl derivatives of nucleic acids is disclosed in non-patent literature 3, and the method has been used to evaluate the toxicity to tumor cells in vitro.

As seen in these prior arts, technologies for stabilizing nucleic acids and for derivatizing nucleic acids themselves are presented. In addition, technologies to label nucleic acids with radioactive iodine etc. are also presented. However, there is no technology that stabilizes the higher-order structure of nucleic acid and makes it detectable.
In view of the above circumstances, it is an object of the present invention to develop a technique capable of stabilizing the higher-order structure of nucleic acid and using it for analysis of nucleic acid structure.

Solution to Problem

As a result of intensive research, we have synthesized guanosine derivatives based on guanosine, one of the nucleobases. The guanosine derivatives have $^{19}$F group as a functional group. In addition, we found that the nucleic acid stabilizes DNA and enables detection by $^{19}$F NMR in a part of the nucleic acid sequence introduced the guanosine derivatives.
The present invention comprises the following components. The first aspect of the present invention is a guanosine derivative represented by Formula 1 below, wherein $R_1$ and $R_2$ are either H and the other is represented by H, OH, $OCH_3$, or F. In addition, $R_3$ is represented by a $^{19}$F functional group for detection, $R_4$ is represented by an amine protecting group or H, and either $R_5$ or $R_6$ is represented by a functional group for introduction into a nucleic acid.

[Chem. 1]

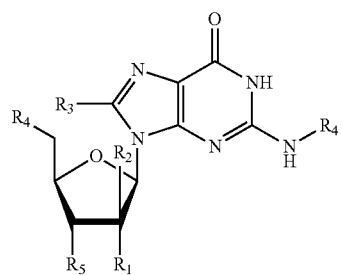

The second aspect of the present invention is a guanosine derivative compound as described in the first configuration, wherein one of $R_1$ and $R_2$ is H, and the other is represented by either H or OH.
The third aspect of the present invention is a guanosine derivative compound as described in the first configuration, wherein $R_3$ is represented by one of the following substituents as shown in Formula 2. (In the formula, n is an integer from 1 to 10, and F is represented as $^{19}$F).

[Chem. 2]

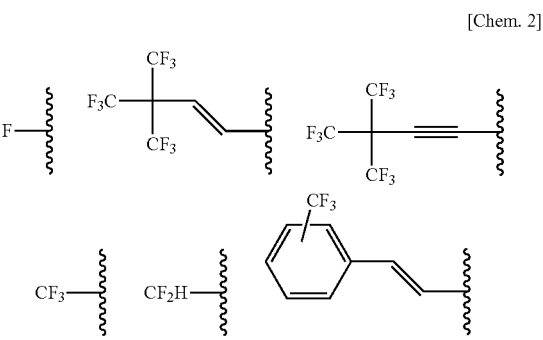

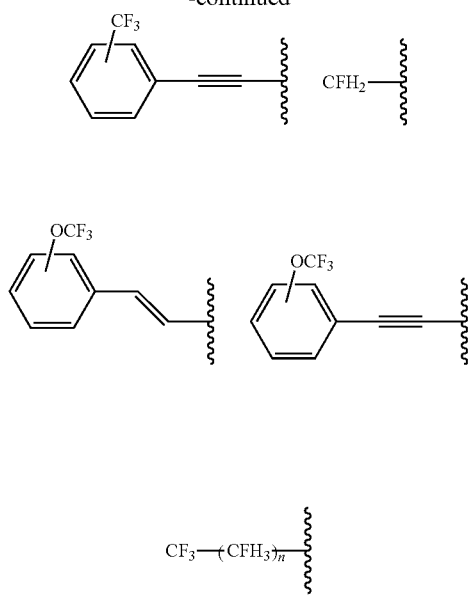

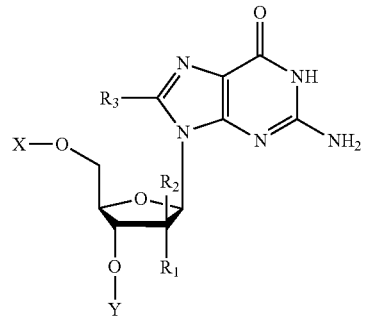

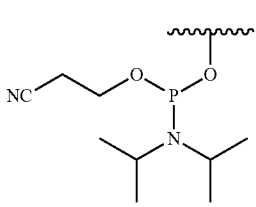

The fourth aspect of the present invention is a guanosine derivative compound as described in any of the first to third configurations, wherein $R_4$ is represented by either a dimethylformamidyl group or an isobutyryl group or an acetyl group or a phenoxyacetyl group or a 4-isopropylphenoxyacetyl group.

The fifth aspect of the present invention is a guanosine derivative compound as described in any of the first to fourth configurations, wherein $R_6$ is represented by a phosphoramidite group.

The sixth aspect of the present invention is a guanosine derivative compound as described in the fifth configuration, wherein $R_6$ is represented by the following formula 3.

[Chem. 3]

The seventh aspect of the present invention is a guanosine derivative compound as described in the fifth or sixth configuration, wherein $R_5$ is represented by either a dimethyltrityl (DMT) group or a monomethyltrityl (MMT) group.

The eighth aspect of the present invention is a guanosine derivative compound as described in any of the first through fourth configurations, wherein $R_5$ is represented by a triphosphate group and $R_6$ is represented by a hydroxyl group.

The ninth aspect of the present invention is a nucleic acid synthesized using one or more of the guanosine derivative compounds described in any of the first through eighth configurations above as part of a constituent sequence, and containing at least one constituent unit represented by the following formula 4 (In the formula, X and Y are represented by ribonucleic acid or deoxyribonucleic acid).

The tenth aspect of the present invention is a stabilization method for improving the stability of a nucleic acid aptamer using the nucleic acid described in the ninth configuration.

The eleventh aspect of the present invention is a method of inhibiting the function of a target protein by specifically binding to the target protein or the like using the nucleic acid described in the ninth configuration as a nucleic acid aptamer.

The twelfth aspect of the present invention is a method for detecting nucleic acids by NMR using the nucleic acid described in the eighth configuration.

The thirteenth aspect of the present invention is a nucleic acid detection method as described in the twelfth configuration, wherein the detection of the nucleic acid taken up into a cell is performed.

The fourteenth aspect of the present invention is a production method for a guanosine derivative compound represented by the following formula 5.

The production method includes the following processes: using guanosine as the starting material, a functional group containing $^{19}F$ for detection ($R_3$) is introduced into the 8-position, an amino group protecting group ($R_4$) is introduced into the amino group of the nucleobase, and a hydroxyl group protecting group ($R_5$) is introduced into the 5' of the sugar backbone, and an amidite group introduction process in which a phosphoramidite amidite group ($R_6$) is introduced into the 3' hydroxyl group of the sugar backbone (In the formula, one of $R_1$ and $R_2$ is H and the other is represented by one of H, OH, $OCH_3$, or F).

[Chem. 4]

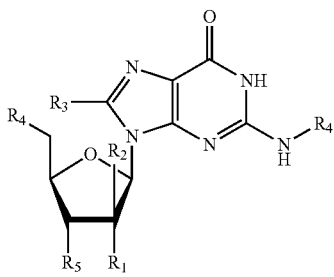

[Chem. 5]

Advantageous Effects of Invention

According to the present invention, it has become possible to provide a technique capable of stabilizing the higher-order structure of nucleic acid and using it for analysis of nucleic acid structure.

BRIEF DESCRIPTION OF DRAWINGS

FIG. 10 shows the results of $^{19}$F NMR and Z-DNA ratio of ODN1 at different NaCl concentrations;

FIG. 11 shows the results of $^{19}$F NMR and Z-DNA ratio of ODN2 and ODN5 at different NaCl concentrations;

FIG. 12 shows the $^{19}$F NMR results of ODN3 and ODN7 by changing the ODN3/ODN7 ratio and reaction temperature;

FIG. 13 shows the $^{19}$F NMR results after culture of HeLa cells in medium containing ODN1 and purification and separation of medium and cells;

FIG. 14 shows the results of anticoagulant activity in an FeCl$_3$-induced rat carotid thrombosis model.

DESCRIPTION OF EMBODIMENTS

Figure 1:
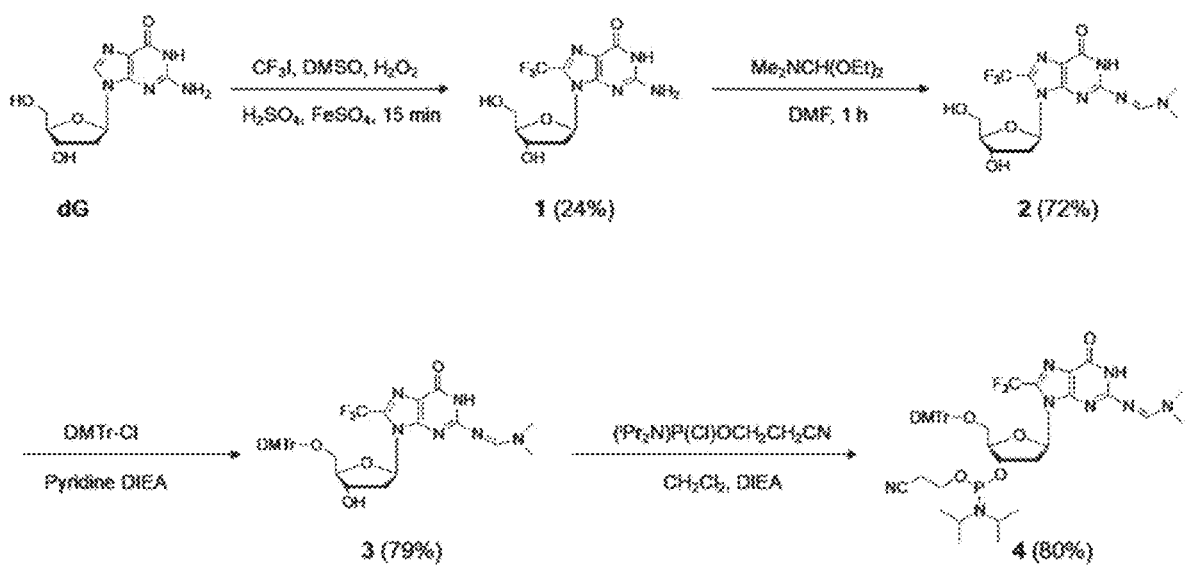
FIG. 1 shows the synthetic scheme of a guanosine derivative.

The guanosine derivative and other compounds of the present invention will be described.

The guanosine derivative in the present invention is represented by formula 6. In other words, the guanosine derivative in the present invention can be incorporated as part of a nucleic acid sequence and functions as a compound equivalent to guanine. In addition, the nucleic acid prepared by introducing the guanosine derivative stabilizes the higher-order structure and enables dynamic detection of the higher-order structure by $^{19}$F NMR.

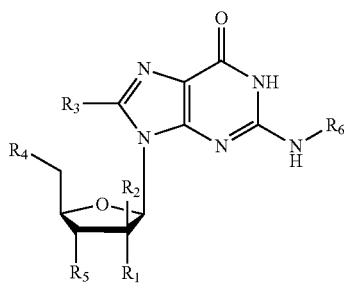

[Chem. 6]

In the formula 6, one of $R_1$ and $R_2$ is H and the other is H, OH, OCH$_3$ or F. In other words, when both $R_1$ and $R_2$ are H, the deoxyguanosine derivative can be introduced as part of the nucleic acid sequence of DNA. When either $R_1$ or $R_2$ is OH, it is a guanosine derivative (non-deoxyguanosine derivative) that can be introduced as part of the nucleic acid sequence of RNA. In addition, when either $R_1$ or $R_2$ is OCH$_3$, it can be introduced into the nucleic acid sequence as a methyl guanosine derivative in which the 2' is methylated. Furthermore, when either $R_1$ or $R_2$ is F, it can be introduced into a part of the nucleic acid sequence as a compound for detection by setting F to $^{18}$F or $^{19}$F.

In the formula 6, $R_3$ is represented by a detection functional group with $^{19}$F. In other words, $R_3$ has $^{19}$F, which enables dynamic detection by $^{19}$F NMR. $R_3$ is not limited to any particular structure, and can have a variety of structures as long as it provides dynamic detection by $^{19}$F and chemical stability.

Typically, a functional group represented by one of the following substituents can be used as $R_3$. In the formula 7, F is represented as $^{19}$F. n is typically represented by an integer from 1 to 10, but preferably by an integer from 1 to 8, more preferably by 1 to 6, especially preferably by 1 to 4, and most preferably by 1 to 3 from the viewpoint of chemical stability.

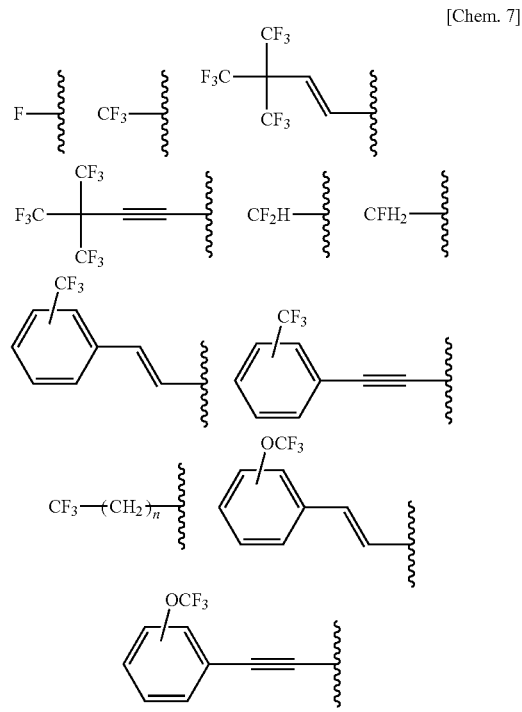

[Chem. 7]

In the formula 6, $R_4$ is represented by an amine protecting group or H, i.e., $R_4$ functions as a protecting group to prevent side reactions in amines, if necessary, in the subsequent reaction process. In the case where $R_4$ is an amine protecting group, there is no need to limit it as long as it prevents such side reactions and can be removed when the nucleic acid is introduced, and various amine protecting groups can be selected and used. A variety of amine protecting groups can be selected and used.

Typically, dimethylformamidyl, isobutyryl, acetyl, phenoxyacetyl and 4-isopropylphenoxyacetyl groups can be used as such $R_4$. In this case, it is preferable to use a phosphoramidite group for $R_6$.

If there is no side reaction in the amine and $R_4$ is set to H, it is preferable to set $R_5$ to a triphosphate group.

In the formula 6, either $R_5$ or $R_6$ is represented by a functional group for introduction into a nucleic acid, i.e., the structure of $R_5$ and $R_6$ is determined by the method used for nucleic acid introduction.

There is no need to limit the method of nucleic acid introduction as long as the guanosine derivative compound of the present invention can be introduced into nucleic acids, and various methods can be used. For example, the method using phosphoramidite (Non-Patent Document 3) and the method using triphosphoric acid (Non-Patent Document 4).

As a method of using a phosphoramidite, $R_6$ can be set to a phosphoramidite group. This has the effect of efficiently introducing the guanosine derivative of the present invention into nucleic acids.

As the phosphoramidite group, various types of phosphoramidite groups that can be introduced into nucleic acids can be used, but preferably, the one represented in formula 8 can be used.

[Chem. 8]

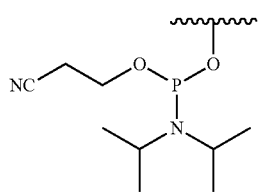

When a phosphoramidite group is used as $R_6$, $R_5$ is represented by a protecting group of hydroxyl group. There is no need to limit $R_5$ as long as it prevents such side reactions and can be removed during nucleic acid introduction, and various hydroxyl protecting groups can be selected for use.

As such $R_5$, dimethyltrityl (DMT) group or monomethyltrityl (MMT) group, etc. can be used.

As a method using triphosphoric acid, $R_5$ can be set to a triphosphate group. This has the effect of efficiently introducing the guanosine derivative of the present invention into nucleic acids. In this case, $R_6$ can be a hydroxyl group.

Guanosine derivatives can be introduced as part of a nucleic acid sequence by a method that depends on the structure of the compound.

As an example, in the case of a guanosine amidite derivative using a phosphoramidite group for $R_6$, the amidite derivative can be introduced into the nucleic acid sequence by a solid-phase synthesis method referred the phosphoramidite method. The prepared nucleic acid can be used after separation and purification using columns, etc., if necessary.

A nucleic acid sequence with guanosine derivatives is represented as a nucleic acid sequence containing at least one of the following structural units.

In other words, the guanosine derivative can be introduced as part of the nucleic acid sequence in one (e.g., the nucleic acids represented in Table 1, ODN1, ODN3, and ODN4) or two or more (e.g., the nucleic acids represented in Table 1, ODN2). The number of introduced nucleic acids can be changed appropriately in consideration of the length of the nucleic acids used and the purpose of the experiment.

In the formula 9, X and Y are represented by ribonucleic acid or deoxyribonucleic acid, and may be chemically modified by methylation or fluorine, as appropriate.

[Chem. 9]

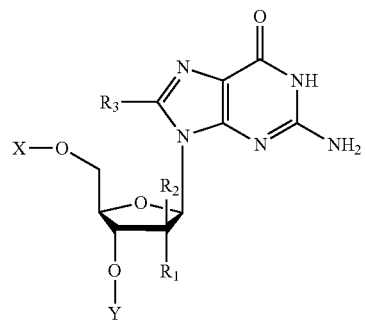

The length of the nucleic acid containing the structural unit of formula 9 need not be limited, and can be adjusted according to the purpose of the experiment. Examples of the length of the nucleic acid are at least three or more, and the upper limit of the length can be selected from 100, 1000, 10,000, 100,000, 1,000,000, 10,000,000, etc.

Nucleic acids prepared by introducing guanosine derivatives can be used for methods to improve the stability of nucleic acid aptamers. In addition, this nucleic acid aptamer can be used for methods of inhibiting the function of a target protein by binding to the functional site of the protein to inhibit it from exerting its function.

Another method for producing guanosine derivatives as another aspect of the present invention is a method for producing guanosine derivatives, which is represented by the following formula 10, and is characterized in that it consists of a process for introducing a functional group for detection, a process for protecting an amino group, a process for protecting a hydroxyl group, and a process for introducing an amidite group (In the formula, one of $R_1$ and $R_2$ is H, and the other is represented by one of H, OH, $OCH_3$, or F).

[Chem. 10]

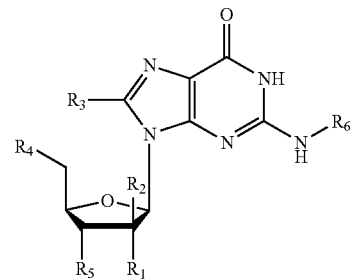

The process for introducing the functional group for detection is a process for introducing a functional group ($R_3$) containing $^{19}F$ at the 8-position using guanosine as a starting material. The process for introducing the functional group for detection does not need to be specifically limited as long as the functional group for detection can be introduced, and various methods can be employed.

For example, 2'-deoxyguanosine is used as a starting material and reacted with trifluoromethyl iodide using dimethyl sulfoxide/sulfuric acid as a solvent in the presence of hydrogen peroxide/iron(II) sulfate to perform trifluoromethylation at position 8 (FIG. 1a).

The amino group protection process is a process to introduce an amino group protecting group ($R_4$) to the amino group of the nucleobase. The amino group protection process does not need to be specifically limited as long as the amino group protection process can be introduced, and various methods can be employed.

As an example of the amino group protection process, the amino group of the base portion of the compound after the introduction of the functional group for detection can be protected with N,N-dimethylformamide diethyl acetal using DMF as a solvent (FIG. 1b).

The hydroxyl group protection process is a process to introduce a hydroxyl group ($R_5$) into the 5' of the sugar backbone. As long as the hydroxyl group can be introduced, there is no need to limit the hydroxyl group protection process, and various methods can be employed.

As an example of the hydroxyl group protection process, the 5' hydroxyl group of the sugar backbone of the compound after the amino group protection process can be protected with 4,4'-dimethoxytrityl chloride in the presence of N,N-diisopropylethylamine using pyridine as a solvent (FIG. 1c).

The amidite group introduction process is a step for introducing a phosphoramidate group ($R_6$) to the 3' hydroxyl group of the sugar backbone. The amide group introduction process does not need to be particularly limited as long as the phosphoramidate can be introduced, and various methods can be employed. As an example of the amidite group introduction process, the 3' hydroxyl group of the sugar backbone is phosphoramidate with 2-cyanoethyldiisopropylchlorophosphoramidite in the presence of N,N-diisopropylethylamine using dichloromethane as a solvent. (FIG. 1d).

In this section, we will use examples to provide further details.

Experiment 1: Synthesis of 8-trifluoromethyl-2'-deoxyguanosine phosphoramidite

1. The synthesis of 8-trifluoromethylguanosine was carried out according to the scheme shown in FIG. 1.
(1) 2'-deoxyguanosine was used as a starting material and trifluoromethylated at position 8 by fluorination reaction with trifluoromethyl iodide in the presence of hydrogen peroxide/iron(II) sulfate using dimethyl sulfoxide/sulfuric acid as a solvent (a, trifluoromethylation, introduction of functional group for detection).
(2) The amino group of the base was protected with N,N-dimethylformamide diethylacetal using DMF as a solvent (b, amino group protection step).
(3) The 5' hydroxyl group of the sugar moiety was protected with 4,4'-dimethoxytrityl chloride in the presence of N,N-diisopropylethylamine in the presence of pyridine (c, 5' hydroxyl group protection step).
(4) The 3' hydroxyl group of the sugar backbone was phosphoramidated with 2-cyanoethyldiisopropylchlorophosphoramidite in the presence of N,N-diisopropylethylamine using dichloromethane as the solvent (d, amidite group introduction step).

Figure 2:
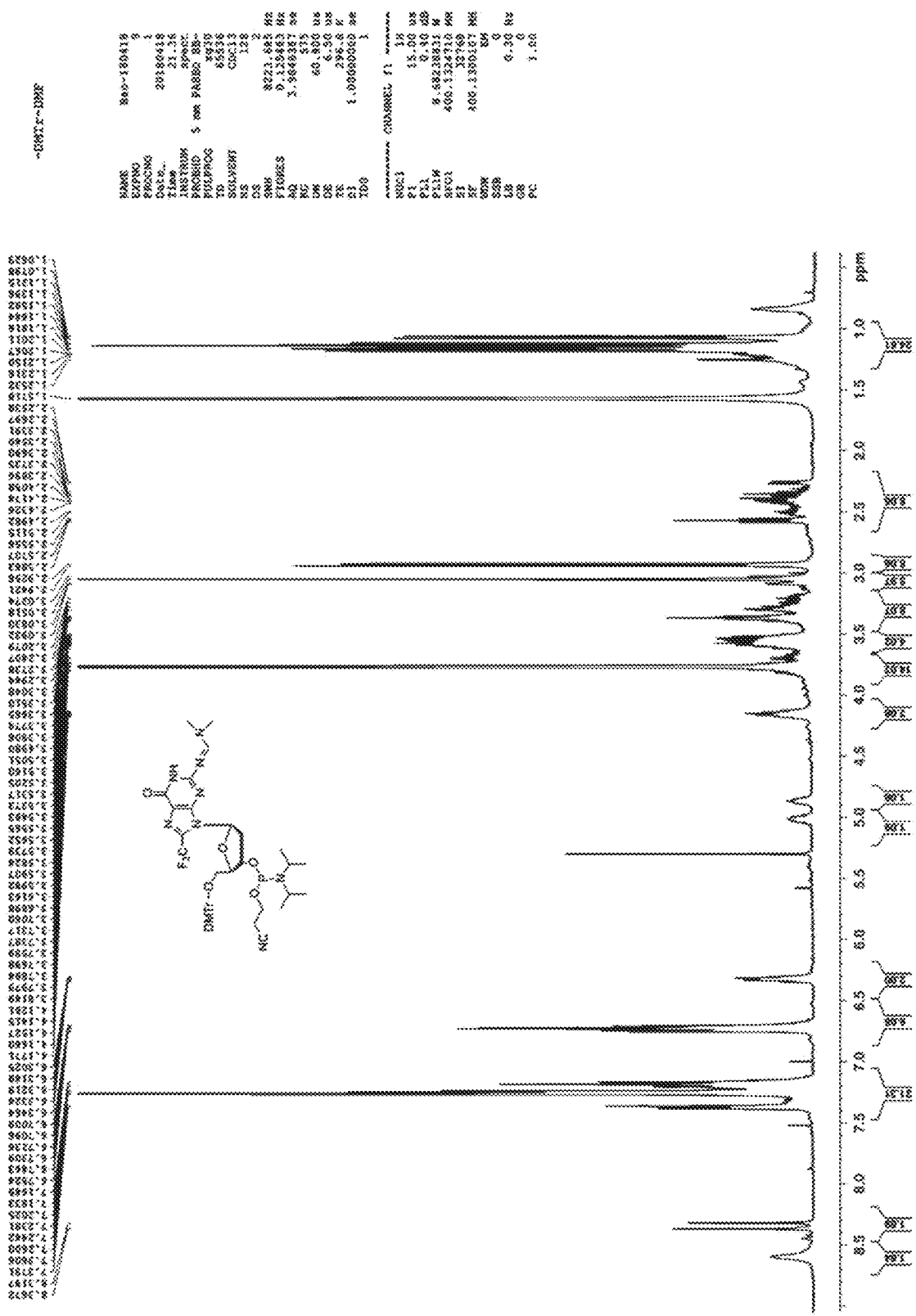
FIG. 2 shows the $^1$H NMR spectrum of a guanosine derivative.
Figure 3:
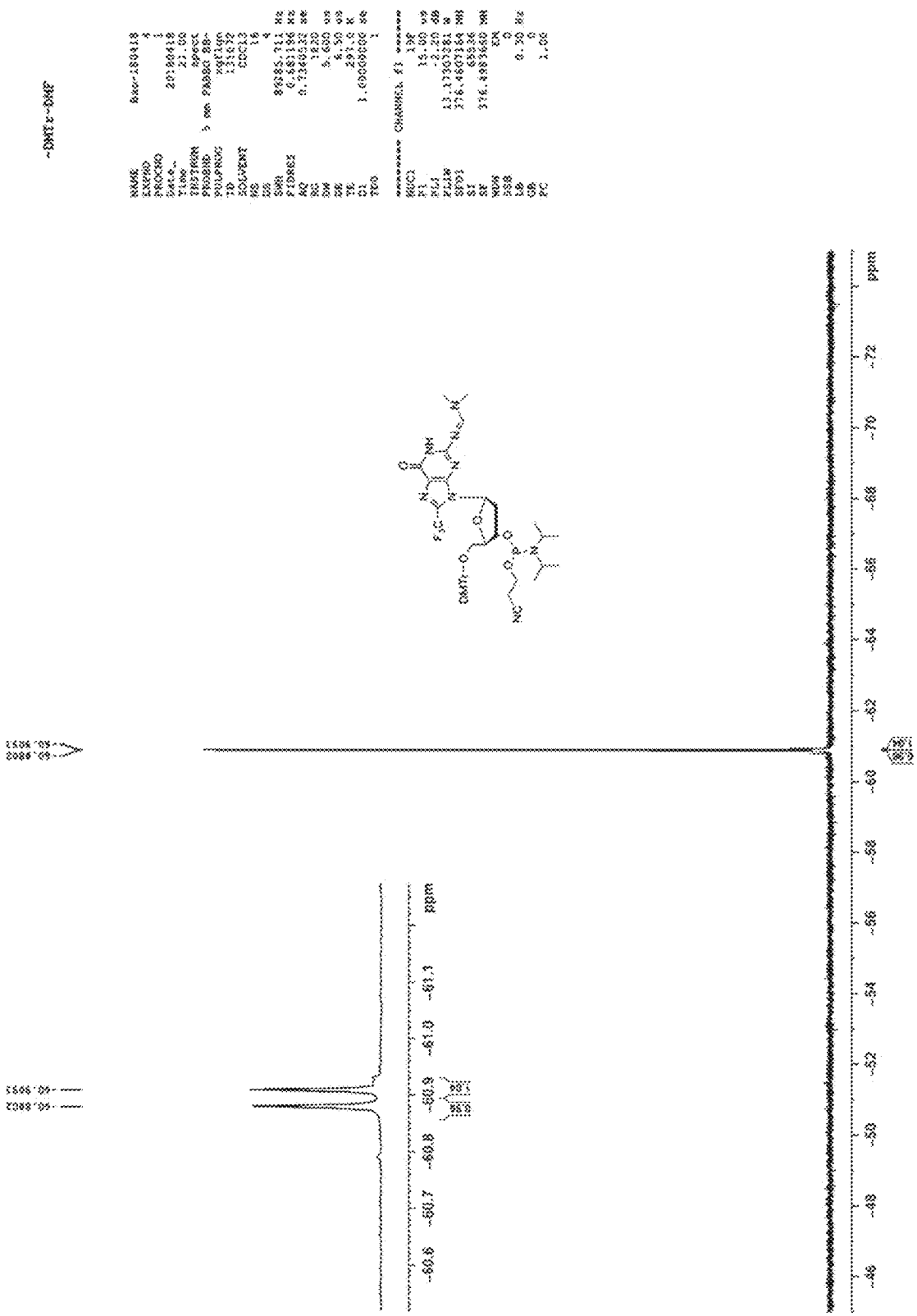
FIG. 3 shows the $^{19}$F NMR spectrum of a guanosine derivative.
Figure 4:
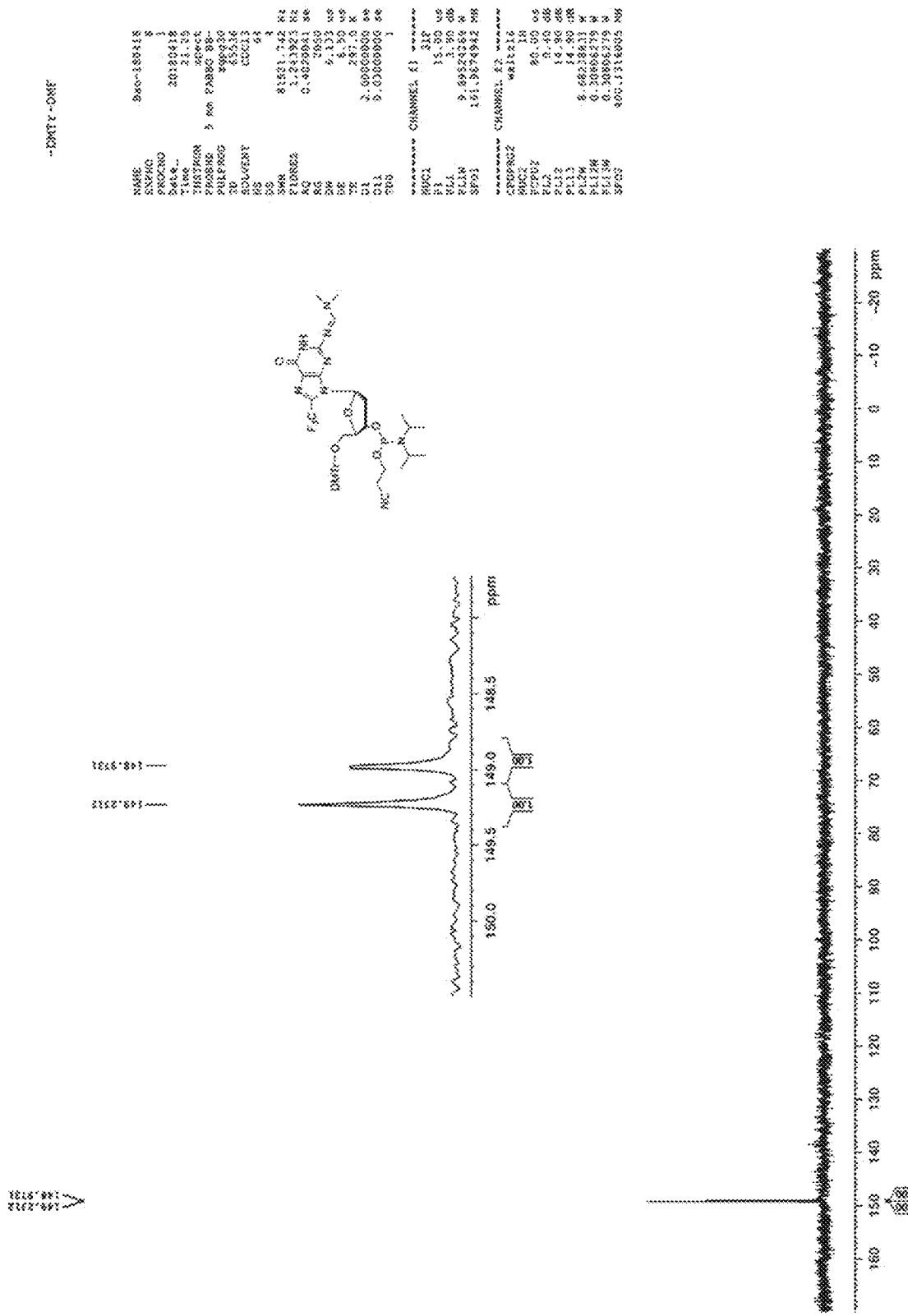
FIG. 4 shows the $^{31}$P NMR spectrum of a guanosine derivative.

2. The $^1H$, $^{19}F$, and $^{31}P$-NMR charts of the synthesized compounds are shown in FIGS. 2-4.

$^1H$-NMR (400 MHz, CDCl$_3$), 8.60 (s, 2H), 8.37 (s, 1H), 8.32 (s, 1H), 7.48 (m, 2H), 7.38-7.16 (m, 20H), 6.75-6.70 (m, 6H), 6.34-6.30 (m, 2H), 5.01 (q, J=2.4 Hz, 1H), 4.87 (q, J=3.7 Hz, 1H), 3.81-3.73 (m, 14H), 3.62-3.50 (m, 4H), 3.39-3.21 (m, 8H), 3.03 (s, 6H), 2.93 (m, 6H), 2.59-2.25 (m, 6H), 1.25-1.06 (m, 24H).

$^{19}F$-NMR (372 MHz, CDCl$_3$) δ 60.88, 60.91.

$^{31}P$-NMR (161 MHz, CDCl$_3$) δ 149.23, 148.97.

Figure 5:
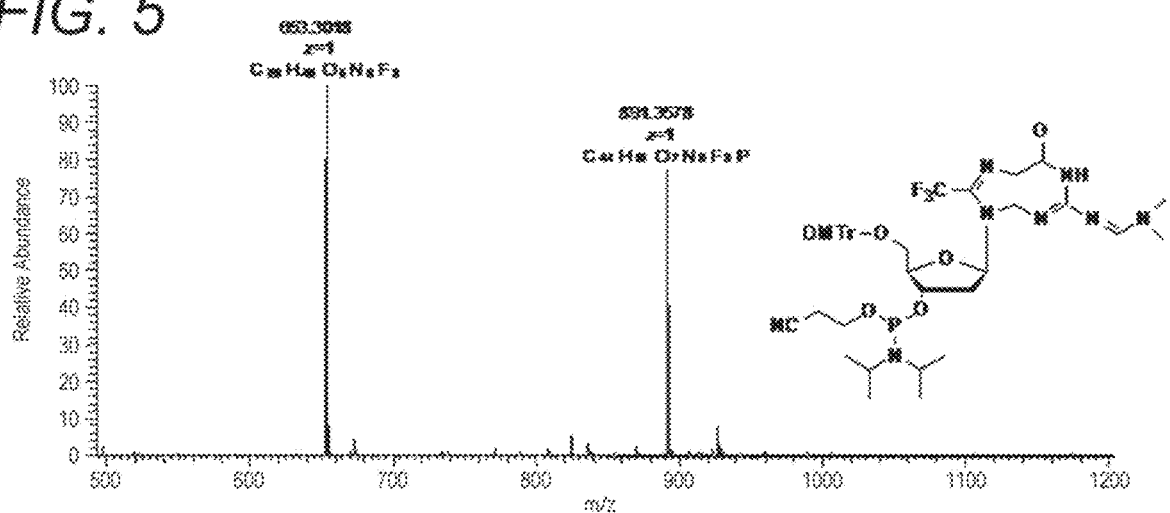
FIG. 5 shows the HRMS (high-resolution MS) spectrum of a guanosine derivative.

3. The HR-Mass results of the synthesized compound 4 are shown in FIG. 5.
(1) A peak consistent with the molecular weight of the putative amidite derivative compound (891.3578) was detected.
(2) The other peak (653.3018) was also consistent with the molecular weight of a possible fragment of the amidite derivative.
4. From these results, it was confirmed that this was the target amidite derivative compound.

Experiment 2: Synthesis of Nucleic Acid Oligomers Containing 8-trifluoromethyl-2'-deoxyguanosine (1) Nucleic acid oligomers containing 8-trifluoromethyl-2'-deoxyguanosine were synthesized by the solid-phase synthesis method by using an automated DNA/RNA synthesizer.
(2) AMA (28% ammonia solution:methylamine=1:1) was added to a CPG (Controlled Pore Glass) carrier, and the oligomer was cleaved.
(3) The AMA solution in which the oligomer was dissolved was incubated at 65° C. for 10 min to deprotect the nucleobase.
(4) After removing the solvent, the oligomers were dissolved in sterilized water and purified using a Glen-Pak cartridge.
(5) The target oligomer was purified by reversed-phase HPLC.
(6) The target oligomer was identified by MALDI-TOF MS.

TABLE 1

Sequences of the synthesized nucleic acid oligomers. In the table, the underlined sites are the sites where the guanosine derivatives of the present invention were introduced.

| DNA sequences | |
|---|---|
| ODN1 (sequence1) | 5'-CGCGCG-3' |
| ODN2 (sequence2) | 5'-CGCACGCG-3' |
| ODN3 (sequence3) | 5'-TAGGGT-3' |
| ODN4 (sequence4) | 5'-GGTTGGTGTGGTTGG-3' |
| ODN5 (sequence5) | 5'-CGCGTGCG-3' |
| ODN6 (sequence6) | 5'-TAGGGT-3' |
| ODN7 (sequence7) | 5'-GGGTTAGGGTTAGGGT-3' |
| ODN8 (sequence8) | 5'-GGTTGGTGTGGTTGG-3' |

TABLE 2

Results of MALDI-TOF MS analysis of ODN1 to ODN4.

| | DNA sequences | Calculated | Found |
|---|---|---|---|
| ODN1 (sequence1) | 5'-CGCGCG-3' | 1858.33 | 1859.21 |
| ODN2 (sequence2) | 5'-CGCACGCG-3' | 2529.42 | 2528.58 |
| ODN3 (sequence3) | 5'-TAGGGT-3' | 1912.34 | 1913.43 |
| ODN4 (sequence4) | 5'-GGTTGGTGTGGTTGG-3' | 4791.78 | 4795.76 |

Experiment 3: Investigation of Stability Using Nucleic Acid Oligomers

Figure 6:
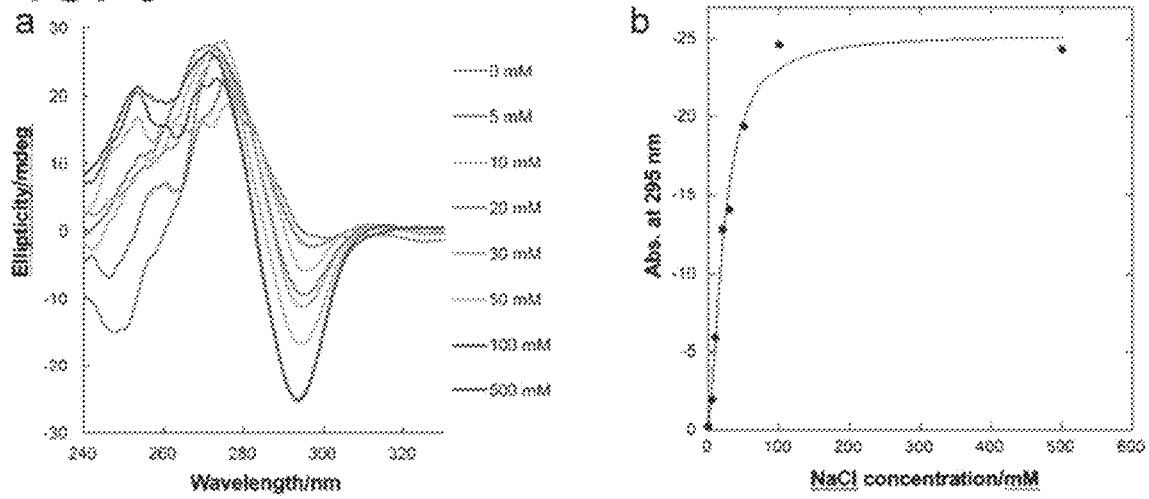
FIG. 6 shows the results of increasing the stability of the nucleic acid structure using ODN1.
Figure 7:
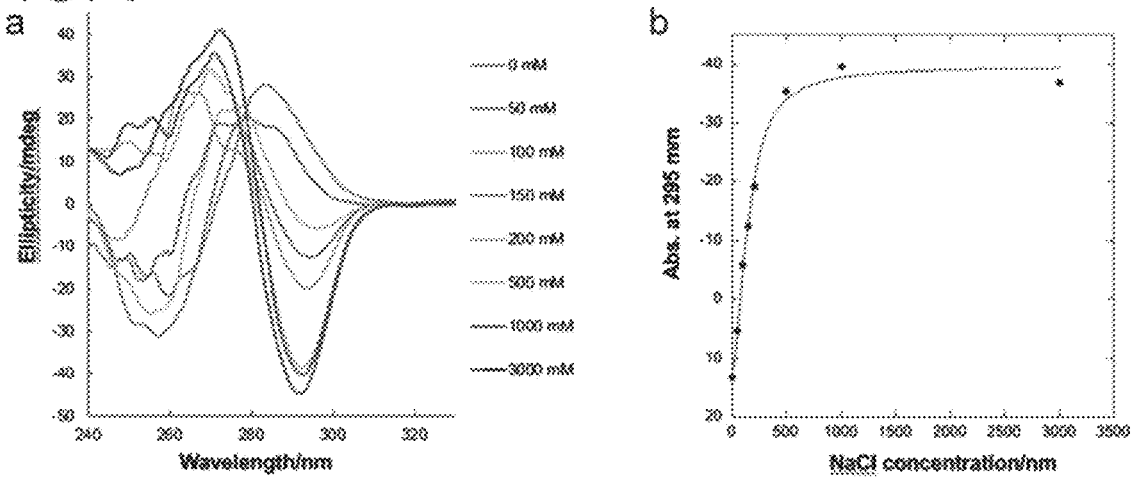
FIG. 7 shows the results of increasing the stability of the nucleic acid structure using ODN2 and ODN5.
Figure 8:
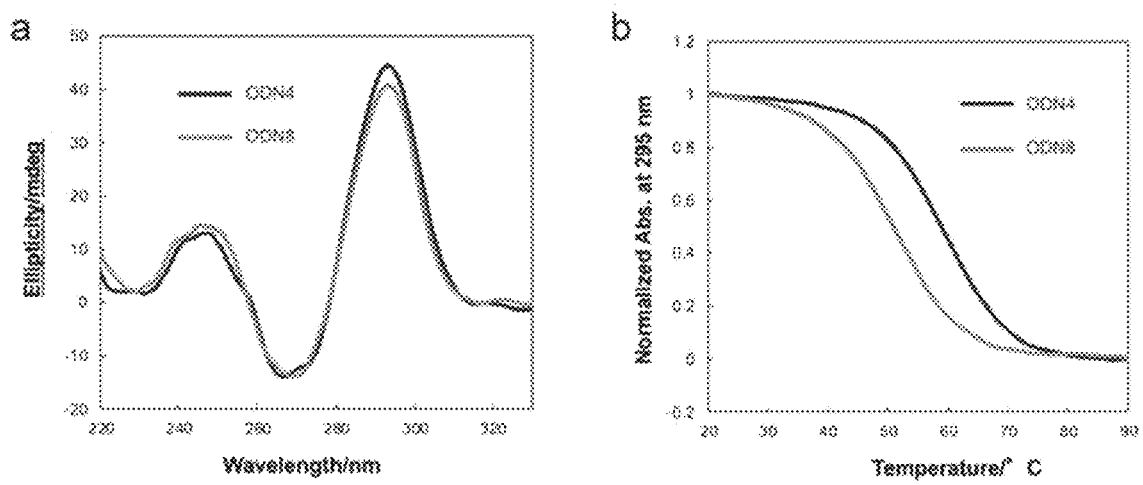
FIG. 8 shows a comparison of the chemical properties of ODN4 (guanosine derivative was introduced) versus ODN8 (natural guanosine was introduced)
Figure 9:
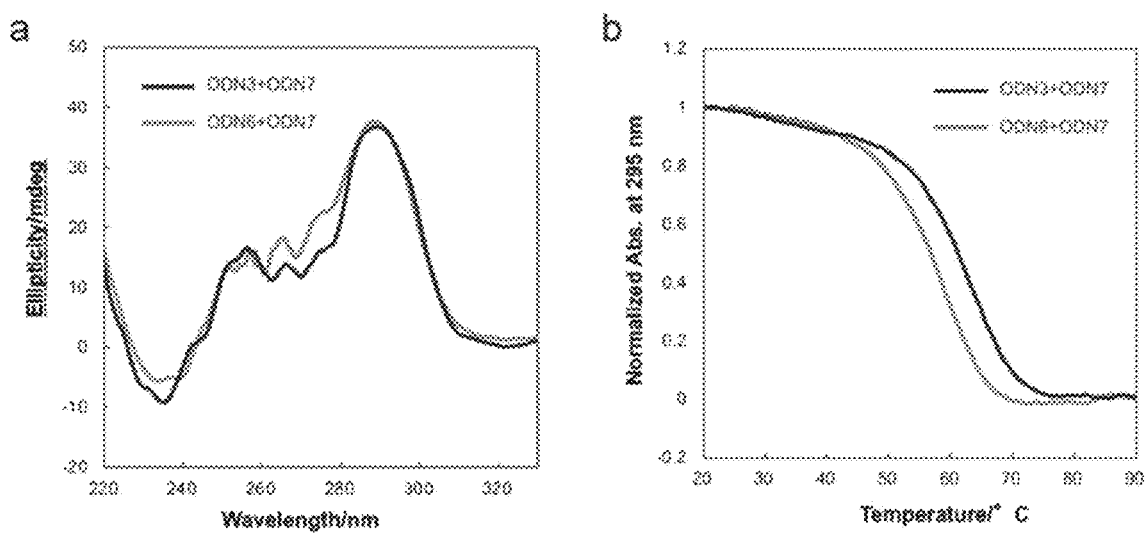
FIG. 9 shows a comparison of the chemical properties of ODN3 (guanosine derivative was introduced) versus ODN6 (natural guanosine was introduced) with ODN7.

1. The stability of the higher-order structure was evaluated by measuring the CD spectra in solution using the nucleic acid oligomers prepared in Experiment 2.
2. The CD results of ODN1 are shown in FIG. 6.
   (1) As the concentration of NaCl in the solution increased, the CD signal at 295 nm became larger in the negative direction.
   (2) In particular, the CD signal plateaued at concentrations of NaCl above 100 mM.
   (3) From these results, it was found that ODN1 with the guanosine derivative of the present invention has a higher-order structure in solution due to stacking of ODN1, and that ODN1 becomes more stable as the salt concentration increases as a left-handed DNA structure.
   (4) In addition, it was confirmed that ODN1 functioned as a nucleic acid oligomer without any problem.
3. The CD results of ODN2 and ODN5 are shown in FIG. 7.
   (1) The CD signal at 295 nm changed from positive to negative at NaCl concentrations of 50 mM and 100 mM, and at concentrations of 100 mM or higher, the spectrum became more negative as the NaCl concentration increased.
   (2) In particular, the CD values plateaued at NaCl concentrations of 500 mM or higher.
   (3) These results indicate that ODN2 with the guanosine derivative stacks with ODN5 in solution to form a higher-order structure, and that ODN2 and ODN5 become more stable as the salt concentration increases as a left-handed DNA structure.
   (4) In addition, it was confirmed that ODN2 functioned as a nucleic acid oligomer without any problem.
4. The results of the comparison of ODN4 and ODN8 are shown in FIG. 8.
   (1) FIG. 8 shows the comparison of thermal stabilities of the higher-order structures of ODN4 (contains a part of guanine with a derivative) and ODN8 (uses natural guanosine) by CD measurement.
   (2) CD signals of ODN4 and ODN8 showed almost similar spectra, indicating that the two aptamer structures are almost same (FIG. 8).
   (3) In addition, the thermal stability of ODN4 is higher than that of ODN8.
5. The results of the comparison of ODN3/ODN7 and ODN6/ODN7 are shown in FIG. 9.
   (1) FIG. 9 shows the comparison of thermal stabilities of the higher-order structures of ODN3 (contains part of a guanine derivative)/ODN7 and ODN6 (uses natural guanosine)/ODN7 by CD measurement.
   (2) CD signals of ODN3/ODN7 and ODN6/ODN7 showed almost similar spectra, indicating that the two aptamer structures are almost same (FIG. 8).
   (3) Furthermore, the thermal stability of ODN3/ODN7 is higher than that of ODN6/ODN7.

Experiment 4: NMR Detection Using Nucleic Acid Oligomers

1. The nucleic acid oligomers produced in Experiment 2 were used for detection by $^{19}$F-NMR.
2. The $^{19}$F-NMR results of using ODN1 are shown in FIG. 10.
   (1) The $^{19}$F signal shifted with increasing NaCl concentration.
   (2) The increase in NaCl concentration caused the steric structure to change from right-handed to left-handed duplex, which was reflected in the shift in the $^{19}$F spectra.
   (3) At NaCl concentrations above 100 mM, the Z-DNA ratio reached a plateau. The duplex was stabilized as an almost left-handed DNA structure.
3. The $^{19}$F-NMR results of using ODN2 and ODN5 are shown in FIG. 11.
   (1) The $^{19}$F signal shifted with increasing NaCl concentration.
   (2) The increase in NaCl concentration caused the steric structure to change from right-handed to left-handed duplex, which was reflected in the shift in the $^{19}$F spectra.
   (3) At NaCl concentrations above 500 mM, the Z-DNA ratio reached a plateau. The duplex was stabilized as an almost left-handed DNA structure.
4. The $^{19}$F-NMR results of using ODN3 and ODN7 are shown in FIG. 12. In this study, we investigated whether ODN3 and ODN7 can form quadruplexes as shown in FIG. 12a.
   (1) As the amount of ODN7 increased with respect to ODN3, the $^{19}$F signal shifted. When the ratio of ODN3 to ODN7 was 1:1, the $^{19}$F spectrum of ODN3 alone completely disappeared (FIG. 12b).
   (2) When the temperature was varied while the ratio of ODN3 to ODN7 was 1:1, the $^{19}$F signal of ODN3 was not detected from 23° C. to 40° C. As the temperature was increased, the $^{19}$F signal of ODN3 increased and the other $^{19}$F signal decreased. At high temperature (60° C.), the $^{19}$F signal completely disappeared.
   (3) From these results, it was confirmed that ODN3 and ODN7 form a higher-order structure, which is considered to be a G-quadruplex. Furthermore, it was confirmed that the G-quadruplexes melted in response to temperature changes and that these phenomena could be applied to dynamic analysis.

Experiment 5: Nucleic Acid Oligomer Detection Using Cells

1. The purpose of this experiment was to investigate whether ODN1 can be detected in cells.
2. ODN1 was added to HeLa cells treated with SLO at a concentration of 3 mM and incubated for 30 minutes. After incubation, the cells were treated with 1 mM CaCl$_2$), and the cells and culture medium (supernatant) were separated and purified, and the signals were detected by $^{19}$F NMR. In addition, Z-DNA and B-DNA were prepared using ODN1 alone, and the signals were detected by $^{19}$F NMR.
3. The $^{19}$F NMR results are shown in FIG. 13.
  (1) The $^{19}$F signal as that of the Z-DNA of ODN1 was observed in the cells and supernatant.
  (2) It was confirmed that ODN1 was taken up into the cells and formed the Z-DNA structure.

Experiment 6. Evaluation of Anticoagulant Activity in an FeCl$_3$-Induced Rat Carotid Thrombosis Model 1. Nucleic acid aptamers, KCl, and potassium phosphate buffer were mixed to prepare solutions with final concentrations of 2 mM, 100 mM, and 20 mM, respectively, followed by annealing.
2. Rats were anesthetized by intraperitoneal administration of 10 mL/kg of three types of mixed anesthetic agents.
3. The jugular vein was detached and exposed through an incision in the rat neck, and 2 μmol/kg of nucleic acid aptamer was administered by intravenous injection.
4. Parafilm and filter paper were placed under the exposed and detached carotid artery. After this, 10 μL of 40% FeCl$_3$ solution was added to the filter paper, and carotid artery injury was induced for 10 min. The injured carotid artery was removed and soaked in formalin solution. The extent of injury was evaluated by HE staining.

The results of anticoagulant activity in an FeCl$_3$-induced rat carotid thrombosis model are shown in FIG. 14.
  (1) Thrombus was observed in the pathological specimens of the carotid artery of mice injected with PBS, and thrombus formation was suppressed in the carotid artery of mice injected with natural TBA. Importantly, almost no thrombus was observed in the carotid arteries of mice intravenously injected with modified TBA.
  (2) Thus, it was confirmed that the modified TBA efficiently inhibited thrombus formation.

The invention claimed is:
1. A guanosine derivative compound represented by the following formula 1

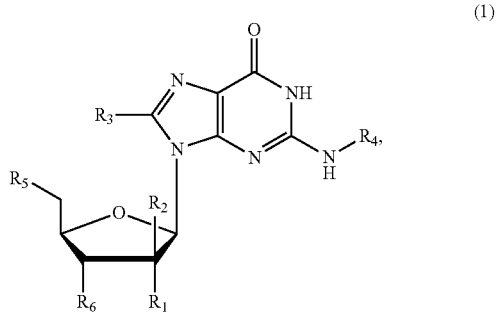

wherein either one of R$_1$ or R$_2$ is H and other one of R$_1$ or R$_2$ is H, OH, OCH$_3$, or F,
R$_3$ is $^{19}$F$_3$C,
R$_4$ is either one selected from the group consisting of a dimethylformamidyl group, an isobutyryl group, an acetyl group, a phenoxyacetyl group and a 4-isopropylphenoxyacetyl group,
R$_5$ is either one a dimethyltrityl group or a monomethyltrityl group, and
R$_6$ is represented by the following formula 3

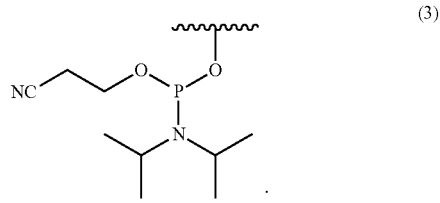 [SMILES: *OP(OCCC#N)N(C(C)C)C(C)C]

2. The nucleic acids synthesized using one or more of the guanosine derivative compounds described in claim 1 as part

SEQUENCE LISTING

<160> NUMBER OF SEQ ID NOS: 2

<210> SEQ ID NO 1
<211> LENGTH: 16
<212> TYPE: DNA
<213> ORGANISM: Artificial Sequence
<220> FEATURE:
<223> OTHER INFORMATION: ODN7

<400> SEQUENCE: 1
gggttagggt tagggt                                              16

<210> SEQ ID NO 2
<211> LENGTH: 15
<212> TYPE: DNA
<213> ORGANISM: Artificial Sequence
<220> FEATURE:
<223> OTHER INFORMATION: ODN8

<400> SEQUENCE: 2
ggttggtgtg gttgg                                               15 of a constituent sequence, and containing at least one constituent unit represented by the following formula 4, wherein X and Y are ribonucleic acid or deoxyribonucleic acid

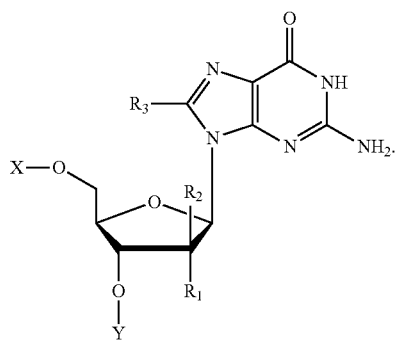

(4)

3. A stabilization method for improving a stability of a nucleic acid aptamer, comprising:
   introducing the guanosine derivative compound described in claim 1 into nucleic acids to obtain a nucleic acid oligomer as the nucleic acid aptamer.

4. A method of inhibiting a function of a target protein, comprising specifically binding the nucleic acids described in claim 2 as a nucleic acid aptamer, to the target protein.

5. A method for detecting nucleic acids by NMR, comprising:
   introducing the guanosine derivative compound described in claim 1 into nucleic acids to obtain a nucleic acid oligomer, and
   detecting the nucleic acid oligomer by $^{19}$F-NMR.

6. The nucleic acid detection method as described in claim 5, further comprising:
   incubating a cell in a medium including the nucleic acid oligomer such that the nucleic acid oligomer is taken up into the cell;
   separating and purifying the cell and a supernatant of the medium; and
   detecting the separated and purified cell by $^{19}$F-NMR.

7. The production method for the guanosine derivative compound described in claim 1, the method comprising:
   using guanosine as the starting material, introducing $^{19}$F$_3$C into the functional group at the 8-position;
   introducing an amino group protecting group represented by the R$_4$ in the formula 1 into the amino group of the nucleobase;
   introducing a hydroxyl group protecting group represented by the R$_5$ in the formula 1 into the 5' of the sugar backbone; and
   introducing a phosphoramidite group represented by the R$_6$ in the formula 1 into the 3' hydroxyl group of the sugar backbone.

8. A stabilization method for improving a stability of a quadruplex, comprising:
   introducing the guanosine derivative compound described in claim 1 into nucleic acids to obtain a first nucleic acid oligomer; and
   forming the quadruplex with the first nucleic acid oligomer and a second nucleic acid oligomer different from the first nucleic acid oligomer.

* * * * *